(12) United States Patent
Selifonov

(10) Patent No.: US 7,211,693 B2
(45) Date of Patent: May 1, 2007

(54) PREPARATION OF LACTIC ACID DERIVATIVES AND THEIR USE

(75) Inventor: Sergey Selifonov, Plymouth, MN (US)

(73) Assignee: Aromagen Corporation, Plymouth, MN (US)

( * ) Notice: Subject to any disclaimer, the term of this patent is extended or adjusted under 35 U.S.C. 154(b) by 0 days.

(21) Appl. No.: 10/523,059

(22) PCT Filed: Jul. 24, 2003

(86) PCT No.: PCT/US03/23119

§ 371 (c)(1),
(2), (4) Date: Oct. 17, 2005

(87) PCT Pub. No.: WO2004/013121

PCT Pub. Date: Feb. 12, 2004

(65) Prior Publication Data

US 2006/0105002 A1    May 18, 2006

Related U.S. Application Data

(60) Provisional application No. 60/400,474, filed on Aug. 2, 2002.

(51) Int. Cl.
C07C 59/08 (2006.01)
C07D 319/12 (2006.01)
A61K 8/18 (2006.01)
A23L 1/00 (2006.01)

(52) U.S. Cl. .................. 562/589; 549/274; 512/12; 426/536

(58) Field of Classification Search .................. None
See application file for complete search history.

(56) References Cited

U.S. PATENT DOCUMENTS 3,280,065 A  10/1966 Langner .............. 260/29.7
3,351,485 A  11/1967 Langner .............. 117/147

OTHER PUBLICATIONS

Andrus et al. Glycolate aldol reactions with boron enolates of bis-4-methoxyphenyl dioxanone. Tetrahedron Letters (2002), 43 (10), 1789-1792.*

Andrus et al., "*Anti*-Selective Glycolate Aldol Additions with an Oxapyrone Boron Enolate," *Org. Lett.*, 2000, 2(19):3035-3037.

Bechtold et al., "Perfectly Alternating Copolymer of Lactic Acid and Ethylene Oxide as a Plasticizing Agent for Polylactide," *Macromolecules*, 2001, 34:8641-8648.

Bischoff, "Ringester aus Äthylenglykol und aus Glycerin," *Chemische Berichten*, 1907, 40:2803-2813.

Burke et al., "Polysubstituted Dihydropyrans via the Enolate Claisen Rearrangement. A Stereocontrolled Route to *C*-Pyranosides," *J. Org. Chem.*, 1984, 49(22):4320-4322.

Deng and Gross, "Ring-opening bulk polymerization of ε-caprolactone and trimethylene carbonate catalyzed by lipase Novozym 435," *Int. J. Biol. Macromol.*, 1999, 25:153-159.

Ebata et al., "Lipase-Catalyzed Transformation of Poly(ε-caprolactone) into Cyclic Dicaprolactone," *Biomacromolecules*, 2000, 1(4):511-514.

Gross et al., "Polyester and polycarbonate synthesis by in vitro enzyme catalysis," *Appl. Microbiol. Biotechnol.*, 2001, 55(6):655-660.

Hall, Jr. and Schneider, "Polymerization of Cyclic Esters, Urethans, Ureas and Imides," *J. Am. Chem. Soc.*, 1958, 80(23):6409-6412.

Hollo, "Untersuchungen über den Einfluβ des Ring-Sauerstoffatoms auf die Reaktionsgeschwindigkeit gewisser Lactone," *Chemische Berichten*, 1928, 61:895-906.

Kobayashi et al., "Lipase-Catalyzed Degradation of Polyesters in Organic Solvents. A New Methodology of Polymer Recycling Using Enzyme as Catalyst," *Biomacromolecules*, 2000, 1(1):3-5.

Kumar and Gross, "*Candida antartica* Lipase B Catalyzed Polycaprolactone Synthesis: Effects of Organic Media and Temperature," *Biomacromolecules*, 2000, 1(1):133-138.

Namekawa et al., "Enzymatic Synthesis of Polyesters from Lactones, Dicarboxylic Acid Divinyl Esters, and Glycols through Combination of Ring-Opening Polymerization and Polycondensation," *Biomacromolecules*, 2000,1(3):335-338.

Namekawa et al., "Lipase-catalyzed ring-opening polymerization of lactones to polyesters and its mechanistic aspects," *Int. J. Biol. Macromol.*, 1999, 25(1-3):145-151.

* cited by examiner

*Primary Examiner*—Sikarl A. Witherspoon
(74) *Attorney, Agent, or Firm*—Fish & Richardson P.C.

(57) ABSTRACT

The present invention relates to preparing lactic acid derivatives that are useful as odorants and monomers for polymer synthesis.

15 Claims, No Drawings

PREPARATION OF LACTIC ACID DERIVATIVES AND THEIR USE

CROSS-REFERENCE TO RELATED APPLICATIONS

This application is a 371 of PCT/US03/23119 filed Jul. 24, 2003, and published as WO 2004/013121 on Feb. 12, 2004.

This application claims priority to U.S. provisional patent application No. 60/400,474, filed Aug. 2, 2002, entitled "Preparation of Lactic Acid Derivatives and Their Use," by S. A. Selifonov, which is hereby incorporated by reference in its entirety.

TECHNICAL FIELD

The present invention relates to preparing lactic acid derivatives that are useful as odorants and monomers for polymer synthesis.

BACKGROUND

Certain 3-methyl-1,4-dioxan-2-ones are known to be useful as odorants.

However, there are general problems with preparation of dioxanone compounds such as associated with use of halogenated raw materials, occurrence of undesired by-products, complexity of synthesis, low yields, and, subsequently high cost. These problems limit application of such compounds as odorants and make them too expensive for polymer synthesis.

SUMMARY

The present invention provides a novel and versatile method of making compounds of formula (1) and (2)

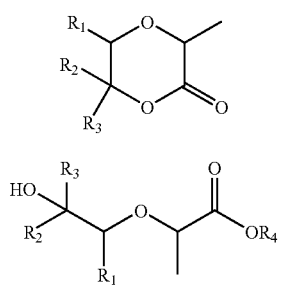

by using lactic acid esters with a free hydroxyl group, and, particularly, ethyl lactate as an inexpensive, safe and abundant renewable raw material available, for example, by means of fermentation of carbohydrates to lactic acid and to ethanol, followed by chemical preparation of the ester. The hydroxyl group of lactate esters is sufficiently reactive to provide for opening of various epoxy compounds, thereby yielding a 2(2'-hydroxyethyl)-propionate ester of formula (2). The latter compounds can be used as such in polymer synthesis or can be further converted to a 3-methyl-1,4-dioxan-2-one via convenient hydrolysis-lactonization sequence or by transesterification. The 3-methyl-1,4-dioxan-2-ones are useful as monomers for polymer synthesis and as odorants. Because many epoxides are produced on a large scale or can be readily prepared by various oxidation methods from a great variety of olefinic compounds, such method is particularly useful and versatile to provide for a library of novel odorant compounds and monomers for polymer synthesis. The type of scent greatly depends on the structure of the epoxide used in the synthesis. Similarly, the properties of polymers or co-polymers depend on the structure of the epoxide. Versatility of the synthetic method of the present invention allows for fine tuning of the desired target properties of the resulting odorants or polymers.

The details of one or more embodiments of the invention are set forth in the description below. Other features, objects, and advantages of the invention will be apparent from the description and from the claims.

DETAILED DESCRIPTION

2(2'-hydroxyethyl)-propionate esters (2) can be conveniently and economically prepared by reaction between an epoxide and a lactate ester according to the following reaction in Scheme 1:

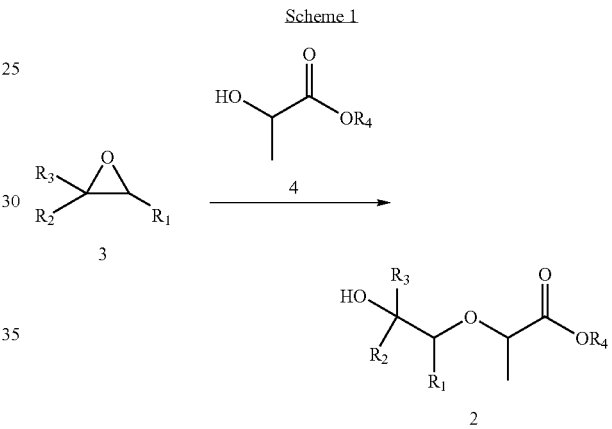

wherein $R_1$, $R_2$, $R_3$ are each independently H, straight or branched alkyl group, straight or branched alkenyl group, carboxyalkyl, carboxyaryl, aromatic group, aromatic-aliphatic group, alkyloxyalkyl, aryloxyalkyl, cycloalkyl, cycloalkenyl, or oxacycloalkyl, or wherein any two of $R_1$, $R_2$, and $R_3$ can form a ring containing 5 to 15 carbon atoms, and wherein any of $R_1$, $R_2$, or $R_3$ optionally contain one oxygen-functional group selected from hydroxyl, carbonyl or protected forms thereof and wherein $R_4$ is a group having between 1 and 50 carbon atoms selected from the group consisting of straight or branched alkyl groups, straight or branched alkenyl groups, cycloalkyl or cycloalkenyl groups, alkyloxyalkyl groups, aromatic groups, aromatic-aliphatic groups, hydroxy-functional alkyl groups, and combinations thereof, or a polymer chain comprising one or more ester or ether, amide bonds.

General conditions useful for a broad range of epoxide opening reactions with lactate esters are described. Such conditions include the use of various catalysts. Typically, such catalysts include various acids. Examples include strong mineral acids, such as sulfuric, hydrochloric, and hydrobromic acids, p-toluenesulfonic acid, camphorosulfonic acid, methanesulfonic acid and the like. Various resins that contain protonated sulfonic acid groups are also useful as they can be easily recovered after completion of the reaction. Boron trifluoride and various complexes of $BF_3$, e.g., in the form of $BF_3$ dietherate, are also useful. Silica, acidic alumina, titania, zirconia and various acidic clays can also be used. However, the nature and amount of the catalyst is not critical. Elevated temperatures may be used to accelerate the reaction with less reactive catalysts, however, the temperature of the reaction mixture is not critical. The amount and type of catalyst depends on the specific chemical composition of the epoxide and lactate ester taken for the reaction and can be readily established by one skilled in the art.

Various co-solvents can be used for the reaction of epoxides with the lactate ester. When co-solvents are used, it is preferred that the solvent not contain a significant amount of water, alcohols, amines, thiols or carboxyl compounds so that competing reactions do not give rise to undesired side products. Various aliphatic and aromatic hydrocarbons, ethers, and esters, including chlorinated compounds, can be used. The use of a co-solvent is particularly beneficial when solid or highly viscous epoxides or lactate esters are used in the synthesis.

To minimize formation of side products, it is advantageous to conduct the reaction between an epoxide and a lactate ester in the presence of sufficient excess of lactate ester, typically with molar ratio of epoxide to lactate ester being in the range of between 1:1.1 to 1:1000, more preferably from 1:1.5 to 1:50. In practice such is easily accomplished by a gradual addition of epoxide to a liquid lactate ester (4), or a mixture of the latter and a suitable co-solvent, and carrying out the reaction until substantially all epoxide has reacted, thereby yielding a mixture of lactate ester (4) and the desired 2(2'-hydroxyethyl)-propionate ester. After reaction, the residual lactate ester can be conveniently distilled out of the higher boiling 2(2'-hydroxyethyl)-propionate ester (1) and reused. The distillation of excess lactate ester is typically carried out at atmospheric pressure or under reduced pressure. Distillations under reduced pressure are preferred because they minimize thermal stress to the reaction products and mitigate formation of side products due to elimination reactions or transesterification.

Any number of lactic acid esters of formula (4) can be used for reaction with epoxides. In a preferred embodiment, use of lower alkyl esters is advantageous because of low cost, high purity and safety, as well as convenience of product separation and re-use of excess of alkyl lactate. In particular, linear or branched alkyl esters of lactate with alcohols having 1–6 carbon atoms are preferred, and ethyl lactate is the most preferred. Both enantiomers of lactate esters can be used in the reaction with epoxides. Racemic or enantiomerically enriched lactates can be used. Use of the (S)-enantiomer of lactate esters, and in particular the (S)-enantiomer of ethyl lactate with enantiomeric purity in excess of 80% is preferred due to low cost and ample availability.

Any number of epoxides of formula (3) can be used. Many epoxides are available commercially in great quantity at low cost. Various methods can be used to prepare epoxides. Olefins can be epoxidized with various reagents, such as peracids and their salts, alkylperoxides, hydrogen peroxide, oxygen, or by the halohydrin method. Various catalysts can be used for epoxidation, including enantioselective or regioselective reactions. Enzymatic or microbiological methods can be used to prepare certain epoxides, and enantiomerically enriched chiral epoxides in particular. For example, styrene monooxygenase or xylene monooxygenase can be used to prepare styrene 1,2-epoxide. Alkane monooxygenase can be used to prepare epoxides from a range of straight chain and branched alkenes, such as 1-hexene, 1-heptene, 1-octene, 1-nonene and like.

The following non-limiting examples of epoxy compounds are provided for the purpose of illustration.

Examples of epoxides include epoxides of linear or branched alkenes, such as ethylene oxide, propylene 1,2-oxide, butylene-1,2- or 2,3-oxide, and 1,2-epoxides of individual or mixed alpha olefins having 5–20 carbon atoms.

Further examples of epoxides include 1,2-epoxides of cyclic alkenes and alkylated cyclic alkenes such as cyclopentene, cyclohexene, cyclooctene, cyclododecene rings, and the like.

Further examples of epoxides include mono- and diepoxy compounds of conjugated and non-conjugated dienes and trienes such as butadiene, isoprene, 1,3- and 1,4-cyclohexadienes, cycloheptatriene, 1,5,9-cyclododecatriene, 1,5-cyclooctadiene, dimethyl-1,5-cyclooctadiene, 4-vinyl-1,2-epoxycyclohexene, norbornene-2,3-oxide, epoxydicyclopentadiene, and the like.

Additional examples of epoxides include epoxides of aromatic alkenes such as styrene-1,2-oxide, indene-1,2-oxide, 3,4-dihydronaphthalene-1,2-oxide, allyl benzene 2,3-oxide, and the like.

Epoxides can be obtained from many natural and synthetic terpenes and terpenoid compounds. Examples of epoxides of this type include limonene-1,2-oxide, 1-menthene-1,2-oxide, 2-menthene-2,3-oxide, isolimonene-2,3-oxide, epoxides of alpha- and beta-phellandrenes, alpha- and beta-pinenes, 2- and 3-carenes, myrcene, ocimene isomers, alpha and gamma terpinenes, and camphene, as well as epoxides of oxygenated terpenoids, such as geraniol, nerol, linalool, terpineol, terpin hydrate, and their esters and ethers, carvone, carveol isomers, piperitol, isopiperitonol, and the like.

It is not necessary to always have epoxides of high purity or defined composition. For example, crude or rectified essential oils or their fractions can be epoxidized to produce a mixture of epoxides. In addition, fractions from the processing of turpentine that contain mixed unsaturated compounds can be epoxidized and used for reaction with lactic acid esters. Other suitable examples include epoxidized materials derived from, or comprising, plant essential oils such as spearmint oil, orange oil, lemon oil, grapefruit oil, cedar oil, vetiver oil, bergamot oil, citronella oil, and the like.

Further examples of epoxides include epoxides from olefins having additional heteroatoms and functional groups. Examples of these compounds include glycidol esters and ethers, as well as epoxides that can be prepared by epoxidation of esters and ethers of unsaturated alcohols. Examples of the latter are epoxides of 2- and 3-hexenol esters and t-butyl ethers. Examples of epoxy compounds having a carboxyl group are glycidic esters such as epoxyacrylate esters, 2,3-epoxycrotonate esters and like. Another set of examples includes epoxides of unsaturated ketones, aldehydes and their ketals or acetals.

Epoxides of conjugated cyclic and acyclic unsaturated ketones and aldehydes, with the carbonyl group optionally protected a ketal or an acetal are particularly useful since they can be readily prepared via aldol condensation of corresponding ketones and aldehydes, followed by epoxidation.

It is also possible for the epoxide and lactate ester to be part of the same molecule, in which case the reaction between the epoxide moiety and the hydroxyl group of the lactate moiety can be carried out intra-molecularly, inter-molecularly, or both, depending on reaction conditions. Thus other examples of compounds are esters of lactic acid and unsaturated alcohols such as 2-alkene-1-ols, and of allyl alcohol in particular. Allyl lactate can be readily prepared from other lactic acid esters by transesterification. For example, transesterification of ethyl lactate, or lactate cyclic dimer (lactide, 2,6-dimethyl-1,4-dioxane-2,5-dione), or polylactate with allyl alcohol in the presence of sodium or potassium alkoxide can be used to produce allyl lactate. The latter can be epoxidized to yield glycidol lactate, which can react intramolecularly to produce 3-methyl-5-hydroxymethyl-1,4-dioxan-2-one (and/or an isomeric cyclic compound 4-oxa-3-methyl-6-hydroxy-ε-caprolactone) or intermolecularly to produce oligomeric or polymeric products.

Compounds of formula (2) can be used to prepare the 3-methyl-1,4-dioxan-2-one compounds having formula (1). The 2(2'-hydroxyethyl)-propionate esters of formula (2) resulting from reaction between an epoxide and a lactate ester can be readily converted to the cyclic ester by one of several methods shown in Scheme 2.

compound can be isolated from the reaction mixture by extraction with appropriate solvent or simply by phase separation.

Preparation of compound (1) by such method results in the formation of free alcohol $R_4OH$ which can be recovered from the reaction mixture, typically by distillation or extraction. The alcohol can subsequently be re-used for preparation of lactic acid ester of formula (4) by a trans-esterification of lactide, or of polylactate, or of other lactate ester, thereby reducing cost of preparation of 3-methyl-1,4-dioxan-2-ones on the industrial scale.

Method (B) is a variation wherein hydrolysis of the compound (2) is carried out by an enzyme, typically by a lipase or esterase. Many enzymes of this type are known and available in commercial quantities. Free or immobilized enzymes can be used. The reaction can be carried out in the presence of a suitable co-solvent. The nature of the enzyme

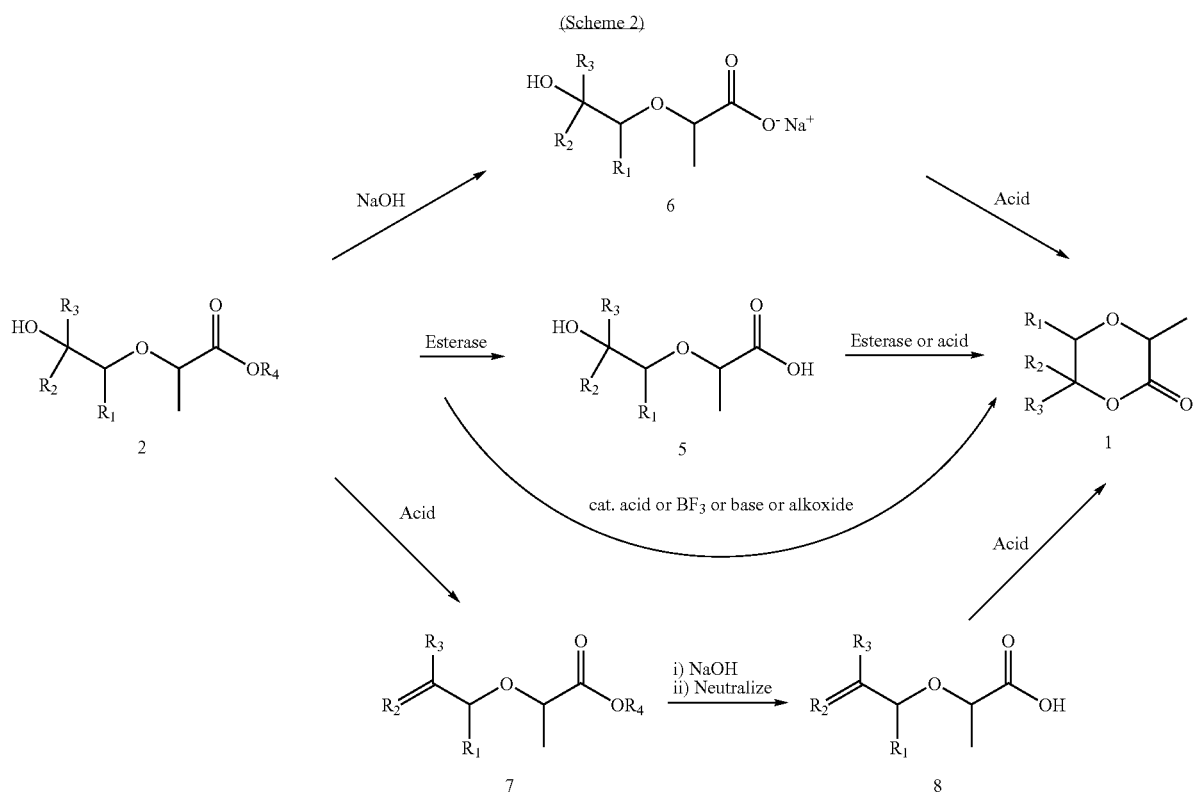

Method (A) comprises two separate reactions. First, the ester of formula (2) is hydrolyzed (saponified) in the presence of sufficient amount of a base, thereby yielding a salt of the 2(2'-hydroxyethyl)-propionate (6), or a mixture of the said salt and free acid (5). Typically, such reaction will be performed by addition of an aqueous solution of an alkali metal hydroxide or an alkali-earth metal hydroxide. Examples include sodium hydroxide, potassium hydroxide, calcium hydroxide, and the like. Sodium hydroxide in water or calcium hydroxide in water are the preferred reagents. After saponification, the reaction mixture is acidified by addition of a sufficient amount of strong acid. Mineral acids such as hydrochloric acid and sulfuric acid are preferred due to low cost. Such acidification results in the formation of the desired the 3-methyl-1,4-dioxan-2-one of formula (1). The is not critical, and many methods in the art are known that allow for improvement of enzyme performance under specific reaction conditions that may be tailored for the specific composition of compound (1). Depending on the precise conditions used, 3-methyl-1,4-dioxan-2-ones can be formed with or without formation of appreciable amounts of the free 2(2'-hydroxyethyl)-propionic acid. Sufficiently thermostable lipases and esterases are preferred as their use allows for continuous distillation of alcohol $R_4OH$ at atmospheric pressure, as such alcohol is formed during the course of reaction.

Method (C) is a variation wherein an internal transesterification is carried out in the presence of catalytic amounts of acid, boron trifluoride, strong base, or alkali metal alkoxide, and in the absence of appreciable amounts of water or other compounds having free hydroxyl groups. Such reaction typically is carried out at elevated temperatures that are sufficient to distill off the alcohol $R_4OH$ from a mixture of compounds (1) and (2), or at room temperatures, when removal of alcohol $R_4OH$ during the transesterification is not desired. Appropriate co-solvents can be used to minimize formation of by-products such as oligomers and polymers. Typical examples of such co-solvents include hydrocarbons or ethers. When method (C) is carried out in the presence of acid or boron trifluoride catalyst, the internal transesterification resulting in the formation of dioxanone (1) can be conducted contemporaneously with the reaction between the epoxide (3) and the ester (4) shown in the Scheme 1, and without isolation of intermediate compound (2).

Method (D) is a variation wherein the 2(2'-hydroxyethyl)-propionic acid ester (2) or free acid (5) is dehydrated under sufficiently acidic conditions and elevated temperatures to yield a compound of formula (7) or a free acid (8). The latter is readily cyclized to yield compound having formula 1. Such method is particularly useful for epoxides of cyclic compounds, and, in particular, for compounds where both $R_2$ and $R_3$ are not hydrogens, and at least one of $R_2$ and $R_3$ has a hydrogen atom capable of elimination under acidic conditions. Depending on the severity of the treatment of compound (2) with acid, and the nature of the epoxide and enantiomeric composition of the lactic ester, such method provides for changes in relative stereoisomeric composition of the resulting cyclic dioxanone of formula (1) at the carbon atom bearing $R_2$ and $R_3$ in particular.

Any of the methods (A), (B), (C), or (D) are practically useful and can be successfully practiced in a continuous operation mode. Methods (B), (C), and (D) are preferred because such methods do not produce large amounts of inorganic salt by-products.

Method A is preferred in the cases where it is desired to obtain a quantity of pure dioxanone material substantially free of ester oligomers, typically represented by linear or cyclic ester oligomers of compounds (1) and (2) with the lactic acid.

As it will be apparent from the examples provided herein below, various quantities of cyclic and/or linear by-product oligomers, comprising esterified fragments of compound (2), are formed during reaction of epoxide (3) with ester (4) and/or during subsequent cyclization reaction leading to compounds of formula (1). The amount and composition of such oligomers depends on the specific conditions employed to obtain compounds (1) and (2), and on the specific structures of epoxide (3) and (4). Typically, when stronger catalyst or increased amount of catalyst, or elevated temperatures or prolonged reaction times are used for reacting compounds (3) and (4), and/or to accomplish conversion of (2) to (1), the amounts of the oligomeric ester products comprising ester fragments of compound (2) are higher. However, if and when any appreciable amounts of such oligomers are formed during synthesis of compounds (1) and (2) by methods described herein, such oligomers are also useful compounds for perfumery, flavor, and polymer applications. Such oligomers can be optionally separated from the dioxanones (1) and/or from hydroxyesters (2), and converted to the dioxanones using transesterification or saponification-lactonization procedures described herein. Alternatively, a mixture comprising compounds (1) and/or (2) and various amounts of cyclic or linear oligomers, can be saponified and then acidified to obtain pure practically pure dioxanones (1).

Another embodiment of the present invention comprises the synthesis of compounds of formula (1) and (2) with epoxides possessing additional hydroxyl groups or optionally protected hydroxyl groups, typically located in a vicinal position to the epoxy group, e.g., epoxides of allylic alcohols or glycidol derivatives. This embodiment is exemplified by the reactions shown in Scheme 3, wherein $R_6$ is H or a protection group selected from ketal, acetal, 2-tetrahydropyranyl, 2-tetrahydrofuranyl, tertiary branched or cyclic alkyl, carboxylic ester, or silyl group having 3 substituents selected from linear or branched alkyl, aryl, and arylalkyl groups.

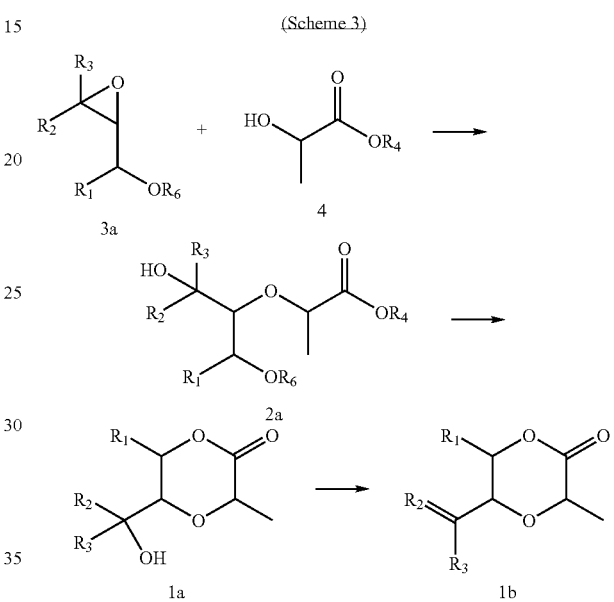

(Scheme 3)

In this embodiment, where both $R_2$ and $R_3$ are not H, the dioxanone ring is preferentially formed with an oxygen atom at the adjacent carbon atom position (compound 1a), and the latter compound can be optionally dehydrated to dioxanone (1b) having a double bond in the side chain at the position C-6. When one of $R_2$ and $R_3$ or both are H, the resulting dioxanone product is a mixture of product isomers exemplified by the formulae (1a) and (1c):

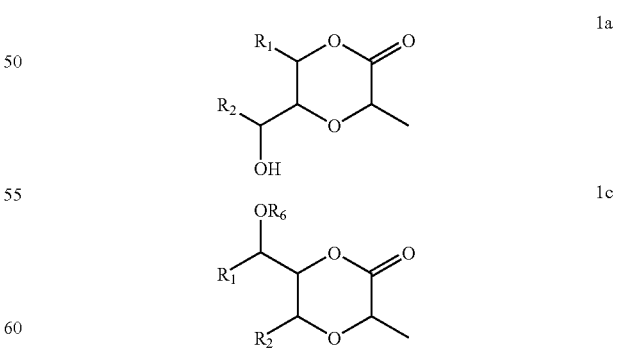

Compounds of general formula (1) prepared from racemic epoxides having chiral centers are typically formed as mixtures of stereoisomers, and, in particular, as mixtures of 3,6-cis and 3,6-trans isomers. Such mixtures of isomers can be used in applications described below, or can be separated, if desired, to obtain substantially pure isomers or compositions with an increased (enriched) amount of one isomer. Methods for resolution of such isomeric mixtures include fractional distillation and biocatalysis using one or more of ordinary esterases or lipases known in the art. Such enzymes typically display moderate to high selectivity under reaction conditions that include or exclude substantial amounts of water from reactions, and can be carried out in a broad range of solvents under conditions that favor hydrolysis, alcoholysis, or transesterification. A compendium of methods for using esterases and lipases for stereoisomer resolution can be found in the textbook by K. Faber (1995, Biotransformations in Organic Chemistry, Spinger-Verlag, ISBN 3-540-58503-6).

Many compounds of formula (1) with total number of carbon atoms less than about 25 have attractive scent characteristics. Depending on the nature of epoxide (5) and the enantiomeric composition of lactic acid ester (4), various types scents of various tenacity can be obtained. A range of scents represented by compounds of formula (1) includes compounds with notes that can be described as floral, fruity, peach, oily, woody, amber, citrus, minty, and cooling. Individual compounds having formula (1) or their mixtures can be used as odorant compounds in various perfumes, hair care products (e.g., shampoos, styling creams, and the like), cosmetics (e.g., lipstick, face powder, and the like), laundry powders, deodorants, candles, air fresheners, soaps, dental care products, cleaning formulations and the like. They can also be used as artificial flavors to impart original taste characteristics in soft drinks, processed fruit products, dairy products such as yogurts, chewing gum, candies, baked goods, tobacco, mouthwash, and the like.

The olfactorily effective amount for a particular dioxanone of formula (1) depends on the precise structure of groups $R_1$, $R_2$, $R_3$, and the stereoisomeric composition of the dioxanone. The potency of the scent and taste can be readily determined by one of ordinary skill in the art by examination of various dilutions of the dioxanone or various concentrations of vapor in the air sample. Such examination can be used as a guide to establish optimal amounts of the dioxanone in a particular fragrance, flavor composition, or formulation.

Compounds of formula (1) and formula (2) can be used to prepare a range of polyester polymers. Such compounds can be used as individual compounds in substantially pure form, or as mixtures of compounds, wherein a mixture is represented by compounds prepared from different epoxides and/or from different enantiomers of lactic esters, and/or from different isomers resulting from alternative nucleophilic opening of the epoxide at carbon atoms bearing either $R_1$ or $R_2$, where applicable. Compounds (1) and (2) can be used as co-monomers with other compounds capable of forming polyester polymers. Non-limiting examples of co-polymers of compounds (1) and (2) include those copolymers that comprise ester fragments derived from lactic acid, glycolic acid, and other 2-hydroxyacids, from 4-hydroxybutyric acid, p-, m-, o-hydroxybenzoic acids, 6-hydroxy-2-naphthoic acid, various aminoacids, as well as combinations of dicarboxylic acids and glycols. Because compounds (1) and (2) can be prepared from a range of epoxides, the precise properties of the resulting polymer can be influenced to a great extent by selection of the particular epoxide used to prepare the compounds. Dioxanones (1) derived from epoxides from alpha-olefins, styrene, allylbenzene or from various glycidyl ethers, offer the greatest flexibility in the precise control of polymer and co-polymer properties, including such properties as melting and softening temperatures, crystallinity, mechanical properties (such as elasticity, stretch/torsion/break resistance), dyeability, hydrophobicity and hydrophilicity, biodegradability, plasticizing properties, metal chelating properties, detergent properties, coagulation and water clarification properties, solvent resistance and solvent swelling, adhesive properties, blending compatibility, and the like.

Methods for preparation of polyesters from carboxylic hydroxyacids, diacids and alcohols, as well as from their esters or lactones, are well known in the art. Such methods are generally applicable to the compounds (1) and (2), and can be used by one skilled in the art without substantial modifications. For example, polymerization of compounds of formulae (1) and (2), and any oligomeric esters thereof, can be accomplished using transesterification under acidic or alkaline conditions, typically under temperatures that allow for distilling out the alcohol $R_4OH$ and/or any water that may be present or formed during the polymerization reaction. The polymerization can be accomplished using a variety of other catalysts, such as transition metal salts of alkanoic acids exemplified by tin 2-ethylhexyloctanoate. Polymerization and co-polymerization of dioxanones of formula (1) can be also accomplished by methods and catalysts described by K. Bechtold, M. A. Hillmyer, and W. B. Tolman. (Macromolecules 2001, 34, 8641–8648), and in references cited therein, for preparation of poly-3-methyl-1,4-dioxan-2-one.

Mixtures of dioxanones (1), hydroxyesters (2), and any ester derivatives thereof that have been obtained by reaction of compounds (3) and (4) can be polymerized to useful co-polymers with lactic acid directly and without separating excess lactic acid ester (4). In this embodiment, the ratio between lactate fragments and 2(2'-hydroxyethyl)-propionate ester fragments derived from dioxanone (1) or hydroxyester (2) depends substantially on the ratio between epoxide (3) and lactic ester (4) used in the reaction leading to the formation of the ether bond between the latter two compounds.

Compounds (1) and (2) can also be co-polymerized with lactide (3,6-dimethyl-1,4-dioxan-2,5-dione) and/or with glycolide (1,4-dioxan-2,5-dione), and/or with 3-methyl-1,4-dioxan-2,5-and/or with tartaric or mesotartaric acid or esters thereof, or graft co-polymerized with polylactic acid, or with polyglycolic acid or with lactate-glycolate copolymers, or with other polymers.

Compounds (1) and (2), and compound (9), described below, and any mixtures thereof, and any ester derivatives or oligomers or polymers comprising fragments of these compounds, can also be polymerized or co-polymerized with other polymers or monomers by using lipases or esterases. Methods for using such enzymes in polyester synthesis and modifications are well known in the art. A description of general enzyme-based polymerization, depolymerization and trans-polymerization methods can be found, for example, in the articles by Gross R. A. et al, (2001, Appl Microbiol Biotechnol. Jun;55(6):655–60), Deng F, and Gross R A. (1999, Int J Biol Macromol. 25(1–3):153–9, Kumar A, and Gross R A. (2000, Biomacromolecules. Spring, 1(1):133–8), Ebata H, et al (2000, Biomacromolecules. Winter;1(4):511–4); Kobayashi S, et al, (2000, Biomacromolecules. Spring;1(1):3–5), Namekawa S. et al. (2000, Biomacromolecules. Fall;1(3):335–8), Namekawa S et al., (1999, Int J Biol Macromol. Jun–Jul, 25(1–3):145–51), and in the references cited therein.

Useful polymers can also be prepared by reacting epoxide (3) and hydroxyester (4) in the compound ratio that favors formation of products of the general formula (9):

(9)

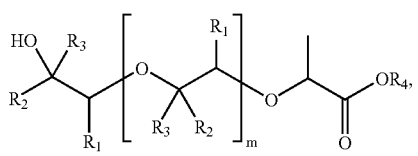

wherein m is an integer having value from 1 to about 50.

Preparation of such compounds is typically accomplished by using a ratio between compounds (3) and (4) in the range from about 50:1 to about 1:1. Preparation of such compounds is typically accompanied by contemporaneous preparation of compounds of formulae (1) and (2). Compounds of formula (9) can be used as co-polymers in the preparation of many polyester-polyether co-polymers that are similar in principal properties to many poly(epoxides) known in the art, and possess additional advantages, in particular, due to the presence of ester bonds in the polyether backbone, such as improved biodegradability in the environment, as compared to poly(epoxides) having continuous polyether backbone uninterrupted by ester bonds.

Polymers and co-polymers comprising fragments of compounds (1), (2) or (9) are also useful for preparing various blends, alloys, or composites with inorganic materials, plasticizers, or with other polymers. In particular, blends and alloys comprising, on one hand, a polymer selected from polylactic acid, polyglycolic acid, or co-polymers comprising fragments of lactic acid, glycolic acid, or poly-(3-hydroxybutyrate) and, on the other hand, polyesters, polyamides, polyepoxides, polyolefins, polystyrene, polyacrylates, polymethacrylates, and polysaccharides, can be prepared by providing fragments of compounds (1), (2), or (9) in at least one polymer or co-polymer. Such blends have improved characteristics and are substantially devoid of phase separation problems, for example, phase separation problems in blends of polylactic acid with polyethylene, polypropylene, or polystyrene

EXAMPLE 1

0.05 ml of racemic styrene epoxide was rapidly added to a solution of 1 microliter of boron trifluoride dietherate in 1 ml of ethyl S(−)lactate and the whole was stirred for 2 minutes at room temperature (about 25° C.). An aliquot (0.01 ml) of the resulting reaction mixture was taken and diluted with ethyl acetate, and was immediately analyzed by GC-MS and GC-FID. The analysis showed complete conversion of styrene oxide to several products. Approximately equal amounts of 3,6-cis-(syn-) and 3,6-trans-(anti-) isomers of 6-phenyl-3-methyl-1,4-dioxan-2-one isomers (formulae 11a and 11b) accounted for about 81% of the reaction products. The percentage number excludes from the calculation, herein and in the subsequent examples, the excess of ethyl lactate used in the reaction; the percentage numbers provided are an approximate indication of yield based on styrene oxide.

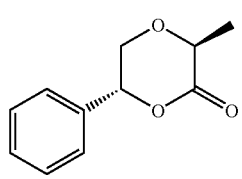
(11a)

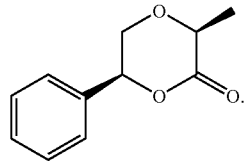
(11b)

The isomers of 6-phenyl-3-methyl-1,4-dioxane-2-one had the following mass-spectra electron ionization mass-spectra at 70 eV, m/z (% abundance):

Trans-isomer (11a):

192 (20, M$^+$), 162 (8), 133 (9), 119 (3), 104 (100), 91 (21), 77 (16), 65 (4), 56 (35).

Cis-isomer (11b):

192 (8, M$^+$), 162 (5), 133 (6), 119 (2), 104 (100), 91 (18), 77 (15), 65 (4), 56 (32).

Approximately 9% of the products were represented by two diastereomers of the hydroxyacid ethyl esters of formula (12):

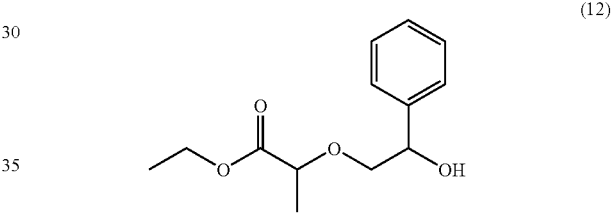
(12)

About 3% of the products were represented by cyclic and linear isomers of formulae (13) and (14):

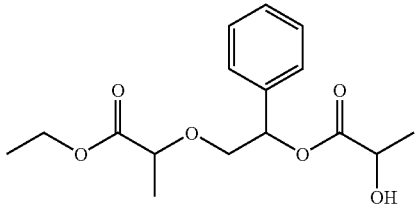
(13)

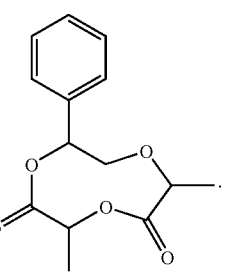
(14)

About 2% of the products were represented by a cyclic dioxanone dimer of formula (15):

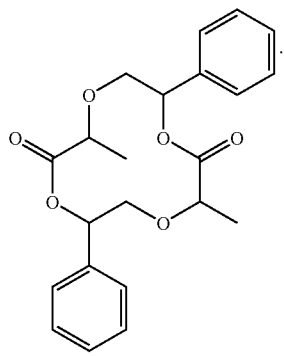

(15)

GC analysis of the same reaction mixture after incubation at room temperature for up to 2 hours with stirring at room temperature showed gradually increased amounts of compounds (13) and (14) due to transesterification reactions in the presence of boron trifluoride etherate, and correspondingly decreased amounts of dioxanones (11a, 11b) and hydroxyesters (12).

EXAMPLE 2

The synthesis was carried out as in example 1, except hexene-1,2-oxide was used instead of styrene oxide. The GC analysis showed complete conversion of hexene 1,2-oxide. Dioxanone isomers having formulae (16a) and 16b) accounted for about 47% of the product mixture. Hydroxyesters of formula (17) accounted for about 32% of the product mixture. Ester-acetal of formula (18) accounted for 9% of the product mixture.

(16a)

(16b)

(16)

(18)

The mass spectrum of dioxanone compound (16a) had a molecular ion with m/z (% abundance) of 172 (13), and characteristic fragment ions 143 (1), 129 (7), 113 (1), 99 (2), 84 (83), 69 (30), 56 (100), 43 (32). The mass spectrum of dioxanone compound (16b) was very similar except the molecular ion was less intense (about 5% of the base peak with m/z 56).

EXAMPLE 3

The synthesis was carried out as in example 1, except cycloxene-1,2-oxide was used instead of styrene oxide. The GC analysis showed complete conversion of cyclohexene 1,2-oxide and the formation of about equal amounts of two isomers of 4-methyl-2,5-dioxabicyclo-[4,4,0]-decan-3-one having formulae (19a) and (19b) that accounted for about 65% of reaction products formed:

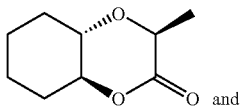

(19a)

and

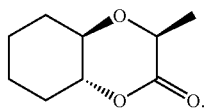

(19b)

These compounds had very similar mass-spectra characterized by molecular ion with m/z (% abundance) of 170 (6), and a series of fragment ions 141 (0.3), 126 (5), 108 (0.5), 98 (5), 82 (85), 67 (100), 54 (31), 41 (21).

The remainder of the product comprised several isomers of compounds having formulae (20), (21) and (22):

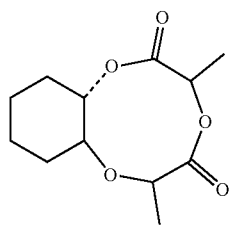

(20)

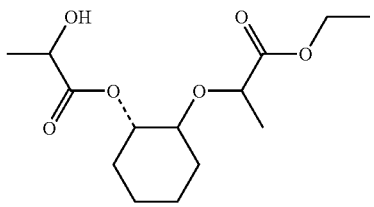

(21)

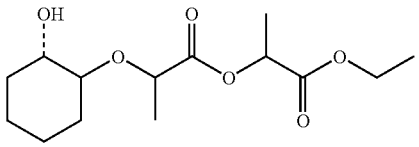

(22)

EXAMPLE 4

The synthesis was carried out as in example 1, except allyl glycidyl ether was used instead of styrene oxide. The product mixture contained about 20% of dioxanone isomers of formula (23)

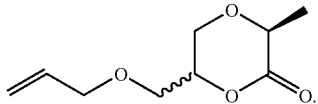
(23)

EXAMPLE 5

The synthesis was carried out as in example 1, except cyclopentene 1,2-oxide was used instead of styrene oxide.

The product mixture contained about 1.5% each of two dioxanone isomers having general formula (24):

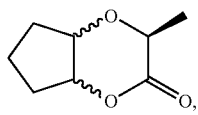
(24)

wherein the wiggled bonds are in a trans-configuration to each other.

The mass-spectra of both isomers of dioxanone (24) had a low intensity molecular ion with m/z (% abundance) 156 (0.5), and fragment peaks with m/z 94 (8), 83 (6), 81 (7), 68 (100), 55 (22), 45 (15).

The product mixture was found to contain predominantly hydroxyesters of formulae (25a) and (25b) in approximately equal amounts, accounting for about 89% of the reaction products:

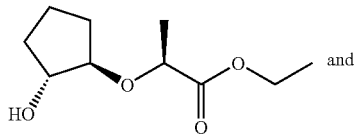
(25a)

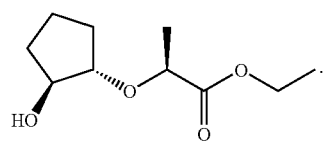
(25b)

Approximately 6% of the reaction products were represented by oligomeric and cyclic oligomeric compounds having formulae (26), (27), (28):

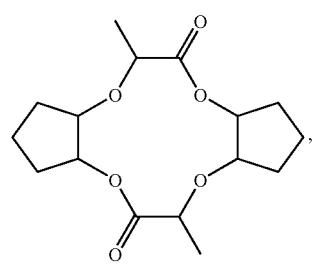
(26)

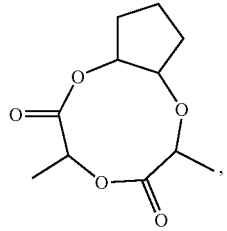
(27)

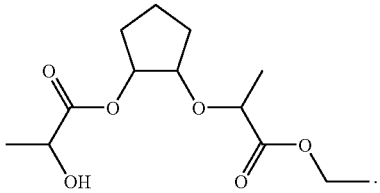
(28)

EXAMPLE 6

The synthesis was carried out as in example 1, except p-nitrophenyl glycidyl ether was used instead of styrene-1,2-oxide and the boron trifluoride dietherate amount was 0.3 microliters. After 5 minutes, the reaction mixture was found to contain about 38% of the initially added amount of p-nitrophenyl glycidyl ether (ca. 62% epoxide conversion). The products found in the reaction mixture comprised about 27% each of two major isomers of dioxanones having formulae (29a) and (29b), and about 2% each of two minor isomers of dioxanones having formulae (29c) and (29d):

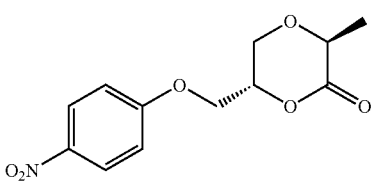
(29a)

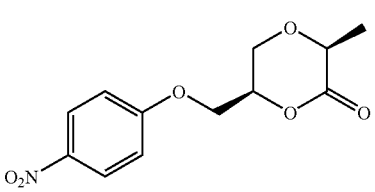
(29b)

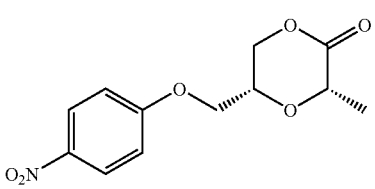
(29c)

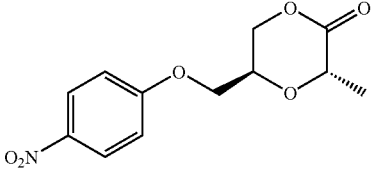
(29d)

The dioxanones of formulae (29a) through (29d) had very similar mass spectra characterized by high intensity molecular ion. For example, dioxanone of formula (29a) was found to have a molecular ion with m/z (% abundance) of 267 (100), and a series of fragment ions 250 (5), 237 (5), 224 (0.5), 207 (0.5), 195 (0.5), 179 (31), 162 (11), 152 (9), 132 (4), 122 (5), 109 (5), 101 (10), 87 (33), 76 (9), 59 (19), 57 (18), 41 (48).

EXAMPLE 7

2 g of DOWEX-50W (strongly acidic cation-exchange resin, protonated form, pre-washed with ethyl lactate) were added to 50 ml of ethyl lactate, and 5.16 g of styrene oxide were added dropwise over 15 minutes to the suspension. The whole was stirred by means of magnetic stirrer for 1 hr at 25° C. After that, the reaction mixture was heated at 55° C. for 3 hours with stirring, cooled to room temperature, filtered, and analyzed by GC-MS and GC-FID. The analysis showed complete conversion of styrene oxide into several products that comprised about 76% of 1:1 mixture of 3,6-syn- and 3,6-anti-isomers of 6-phenyl-3-methyl-1,4-dioxan-2-one (11a and 11b), about 6% of hydroxyesters (12), about 1% of ester ketal having formula (30),

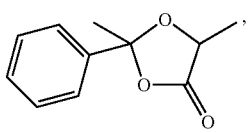

about 2 (%) of ester acetal having formula (31),

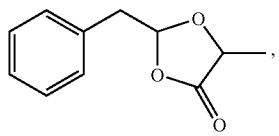

and about 11% of linear and cyclic esters of formulae (13) and (14).

Approximately 42 ml of practically pure ethyl lactate was distilled out the reaction mixture by heating to about 160° C. at atmospheric pressure. The remaining pale yellow viscous liquid was saponified with 30 ml of 20% sodium hydroxide in water by heating for 2 hours at 95° C. with stirring. The resulting solution was cooled to room temperature, washed 3 times with 20 ml of methyl tert-butyl ether, and filtered. The filtered solution was acidified, while being maintained on the ice bath (4–5° C.) and stirred, by dropwise addition of 20% sulfuric acid in water until pH about 2–3 was reached. The acidified solution was extracted 4 times with 30 ml of ethyl acetate, the extracts were combined, dried over anhydrous sodium sulfate, and the solvent was removed under reduced pressure, to yield 7.60 g of pale-yellow clear oil. The crude product was analyzed by GC-MS and GC-FID and found to contain about 80% of 1:1 mixture of 3,6-syn- and 3,6-anti-isomers of 6-phenyl-3-methyl-1,4-dioxan-2-one (11a and 11b), and about 20% of the cyclic dimer product having formula (15).

An analytical sample of practically pure 3,6-syn- and 3,6-anti-isomers of 6-phenyl-3-methyl-1,4-dioxan-2-one of 1:1 mixture was prepared by vacuum distillation. The mixture of syn- and anti-6-phenyl-3-methyl-1,4-dioxan-2-ones was found to possess a powerful and tenacious unusual floral-honey-rose-balsamic-sweet scent with a note of pleasant bitterness.

EXAMPLE 8

The synthesis was carried out as in example 7, except 5.1 g of hexene 1,2-oxide was used instead of styrene 1,2-oxide. The synthesis yielded about 6.2 g of clear colorless oil that was found to contain about 92% of dioxanones of formula (16a) and (16b). The mixture of compounds had an oily-fruity odor reminiscent of peach.

EXAMPLE 9

The synthesis was carried out as in example 7, except 5.05 g of cyclohexene-1,2-oxide was used instead of styrene 1,2-oxide. The synthesis yielded about 6.9 g of clear colorless oil that was found to contain about 96% of dioxanones (19a) and (19b), and about 2% of isomers of cyclic esters of formula (32):

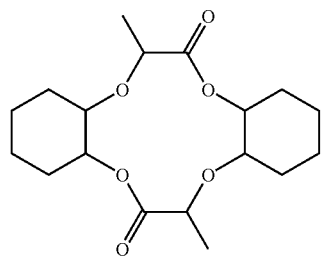

The resulting material is found to have a characteristic powerful floral odor reminiscent of castoreum flower.

A number of embodiments of the invention have been described. Nevertheless, it will be understood that various modifications may be made without departing from the spirit and scope of the invention. Accordingly, other embodiments are within the scope of the following claims.

What is claimed is:
1. A method for making a compound having the formula:

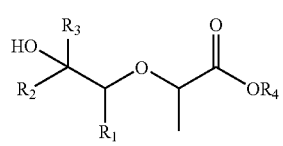

wherein $R_1$, $R_2$, $R_3$ are each independently H, straight or branched alkyl group, straight or branched alkenyl group, carboxyalkyl, carboxyaryl, aromatic group, aromatic-aliphatic group, alkyloxyalkyl, aryloxyalkyl, cycloalkyl, cycloalkenyl, or oxacycloalkyl or wherein any two of $R_1$, $R_2$, and $R_3$ can form a ring containing 5 to 15 carbon atoms, and wherein any of $R_1$, $R_2$, or $R_3$ optionally contain one oxygen-functional group selected from hydroxyl, carbonyl or protected forms thereof, and wherein $R_4$ is a group having between 1 and 50 carbon atoms selected from the group consisting of straight or branched alkyl groups, straight or branched alkenyl groups, cycloalkyl or cycloalkenyl groups, alkyloxyalkyl groups, aromatic groups, aromatic-aliphatic groups, hydroxy-functional alkyl groups, and combinations thereof or a polymer chain comprising one or more ester or ether, or amide bonds, said method comprising:

a) providing an epoxide of formula (3):

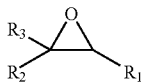

(3)

and b) reacting the epoxide with a lactic acid ester of formula (3):

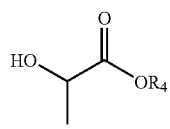

(4)

where the epoxide and ester are in the form of separate molecules or part of the same molecule, thereby providing the compound of formula (2).

2. A method of claim 1 wherein the reaction between the epoxide and the lactic acid ester is carried out in the presence of a catalyst selected from the group comprising boron trifluoride catalysts, acid catalysts, and combinations thereof.

3. A method of claim 1 wherein the reaction between the epoxide and the lactic acid ester is carried out in the presence of excess lactic acid ester, with the molar ratio between the epoxide and the ester being between approximately 1:1.1 to 1:1000.

4. A method of claim 1 wherein the lactic acid ester is glycidyl lactate.

5. A method of claim 1 wherein the reaction between the epoxide and the lactic acid ester is conducted in the presence of a co-solvent.

6. A method of claim 1 further comprising cyclizing the compound of formula (2) to produce a compound having the formula:

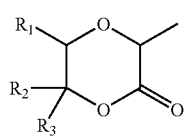

(4)

wherein $R_1$, $R_2$, $R_3$ are each independently H, straight or branched alkyl group, straight or branched alkenyl group, carboxyalkyl, carboxyaryl aromatic group, aromatic-aliphatic group, alkyloxyalkyl, aryloxyalkyl, cycloalkyl, cycloalkenyl, or oxacycloalkyl, or wherein any two of $R_1$, $R_2$, and $R_3$ can form a ring containing 5 to 15 carbon atoms, and wherein any of $R_1$, $R_2$, or $R_3$ optionally contain one oxygen-functional group selected from hydroxyl carbonyl or protected forms thereof.

7. A method as claimed in claim 6, wherein cyclization is carried out by saponifying the 2-(2'-hydroxyethyl)propionate ester of formula (2), followed by acidification.

8. A method as claimed in claim 6 wherein cyclization is carried out by transesterifying the 2-(2'-hydroxyethyl)propionate ester of formula (2) in the presence of a catalyst.

9. A method as claimed in claim 8 wherein cyclization is carried out by treating the 2-(2'-hydroxyethyl)propionate ester with catalyst acid or boron trifluoride to eliminate water, followed by hydrolysis of the ester and acidification.

10. A method of claim 1 wherein the compound of formula (2)

cyclizes in situ to form a compound having the formula:

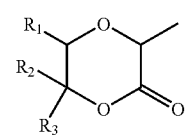

(1)

wherein $R_1$, $R_2$, $R_3$ are each independently H, straight or branched alkyl group, straight or branched alkenyl group, carboxyalkyl, carboxyaryl aromatic group, aromatic-aliphatic group, alkyloxyalkyl, aryloxyalkyl, cycloalkyl, cycloalkenyl, or oxacycloalkyl, or wherein any two of $R_1$, and $R_2$, and $R_3$ can form a ring containing 5 to 15 carbon atoms, and wherein any of $R_1$, $R_2$, or $R_3$ optionally contain one oxygen-functional group selected from hydroxyl carbonyl or protected forms thereof.

11. A method as claimed in claim 6 wherein cyclization is carried out by exposing the 2-(2'-hydroxyethyl)propionate ester to an enzyme selected from the group consisting of lipases, esterases, and combinations thereof.

12. A compound having the formula:

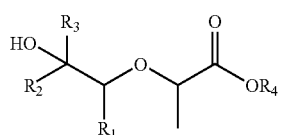

(2)

wherein $R_1$, $R_2$, $R_3$ are each independently H, straight or branched alkyl group, straight or branched alkenyl group, carboxyalkyl, carboxyaryl, aromatic group, aromatic-aliphatic group, alkyloxyalkyl, aryloxyalkyl, cycloalkyl, cycloalkenyl, oxacycloalkyl, or wherein any two of $R_1$, $R_2$, and $R_3$ form a ring containing 5 to 15 carbon atoms, and wherein any of $R_1$, $R_2$, or $R_3$ optionally contain one oxygen-functional group selected from hydroxyl, carbonyl or protected forms thereof, and wherein $R_4$ hydrogen or a group having between 1 and 50 carbon atoms selected from the group consisting of straight or branched alkyl groups, straight or branched alkenyl groups, cycloalkyl or cycloalkenyl groups, alkyloxyalkyl groups, aromatic groups, aromatic-aliphatic groups, hydroxy-functional alkyl groups, and combinations thereof, or a polymer chain comprising one or more ester or ether, or amide bonds.

13. A compound having the formula:

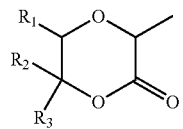
(1)

wherein $R_1$, $R_2$, $R_3$ are each independently H, straight or branched alkyl group, straight or branched alkenyl group, carboxyalkyl, carboxyaryl aromatic group, aromatic-aliphatic group, alkyloxyalkyl, aryloxyalkyl cycloalkyl, cycloalkenyl, oxacycloalkyl, or wherein any two of $R_1$, $R_2$, and $R_3$ form a ring containing 5 to 15 carbon atoms, and wherein any of $R_4$, $R_2$, or $R_3$ optionally contain one oxygen-functional group selected from carbonyl or protected form thereof, with the proviso that:

a) where $R_2=R_3=H$, $R_1$ cannot be methyl or H,
b) where $R_1=R_2=H$, $R_3$ cannot be methyl or ethyl,
c) where $R_3=H$, and $R_1$ and $R_2$ form a cyclohexane or norbornene ring, at least one additional carbon atom, oxygen atom, or double bond must be present in the structure of $R_1$ or $R_2$.

14. A composition comprising a base material and an amount of a compound according to claim 13 effective to impart a fragrance or a flavor to the base material.

15. A method of imparting a fragrance or a flavor to a base material comprising combining the base material with an effective amount of a compound according to claim 13.

* * * * *